United States Patent [19]

Matson

[11] 4,404,065
[45] Sep. 13, 1983

[54] ELECTROCHEMICAL DETECTION SYSTEM AND METHOD OF ANALYSIS

[75] Inventor: Wayne R. Matson, Ayer, Mass.

[73] Assignee: Enviromental Sciences Associates, Inc., Bedford, Mass.

[21] Appl. No.: 111,917

[22] Filed: Jan. 14, 1980

[51] Int. Cl.³ .............................................. G01N 27/30
[52] U.S. Cl. .................................. 204/1 T; 73/61.1 C; 204/411; 422/70; 436/161
[58] Field of Search ................ 204/195 R, 1 T, 195 B, 204/411; 73/61.1 C; 23/230 R; 422/70; 436/161

[56] References Cited

U.S. PATENT DOCUMENTS

| | | | |
|---|---|---|---|
| 3,327,204 | 6/1967 | Hillier et al. | 204/195 R X |
| 3,352,643 | 11/1967 | Ando et al. | 23/230 R |
| 3,556,950 | 1/1971 | Dahms | 204/1 T |
| 3,594,294 | 7/1971 | Pretorius et al. | 204/180 G |
| 3,649,498 | 3/1972 | Pretorius et al. | 204/180 G |
| 3,706,381 | 12/1972 | Joynes et al. | 210/198 C |
| 3,759,816 | 9/1973 | Pretorius et al. | 204/299 |
| 3,856,471 | 12/1974 | Winitz et al. | 23/230 B X |
| 3,902,848 | 9/1975 | Juvet et al. | 23/230 R |
| 3,920,398 | 11/1975 | Small | 23/230 R |
| 3,925,019 | 12/1975 | Small et al. | 23/230 R |
| 3,967,931 | 7/1976 | Juvet et al. | 23/230 PC |
| 3,997,836 | 12/1976 | Haruki et al. | 324/64 |
| 4,014,793 | 3/1977 | Tesarik et al. | 210/198 C |
| 4,036,704 | 7/1977 | Takata | 204/1 T |
| 4,059,406 | 11/1977 | Fleet | 23/230 R |
| 4,206,027 | 6/1980 | Schindler et al. | 204/195 R |

FOREIGN PATENT DOCUMENTS

| | | | |
|---|---|---|---|
| 1262046 | 2/1968 | Fed. Rep. of Germany | 204/195 R |
| 2533943 | 2/1976 | Fed. Rep. of Germany | 204/195 R |
| 2327537 | 5/1977 | France | 204/195 R |
| 1194376 | 6/1970 | United Kingdom | |
| 1517697 | 7/1978 | United Kingdom | 204/195 R |

OTHER PUBLICATIONS

Donald T. Sawyer et al., "Experimental Electrochemistry for Chemists", pp. 34-48 (1974).
H. F. Osswald et al., Chimia, 31, No. 2, (1977).
D. G. Swartzfager, Anal. Chem., vol. 48, No. 14, pp. 2189-2192, (1976).

Primary Examiner—G. L. Kaplan
Attorney, Agent, or Firm—Hayes, Davis & Soloway

[57] ABSTRACT

An electrochemical detection apparatus is provided. The apparatus comprises a flow-cell having at least one active testing electrode, at least one reference electrode, and at least one counter electrode. Each electrode comprises a liquid impervious solid body having a bore extending therethrough with the electrode active surface located in the bore. The electrodes are arranged in a stack, electrically insulated from one another with their respective bores aligned so as to define a flow channel through which liquid to be detected can be passed. In a preferred embodiment of the invention at least one of the reference electrodes is actively driven to supply a stable reference potential against which other electrochemical responses can be measured. Various electrochemical responses are achieved by varying the construction, number and arrangement of electrodes in the stack, and the potentials applied to the electrodes. The detection apparatus has particular utility for use in monitoring chromatographic eluant.

68 Claims, 18 Drawing Figures

ELECTROCHEMICAL DETECTION SYSTEM AND METHOD OF ANALYSIS

The present invention relates to electrochemical analysis, and more particularly to new method and apparatus for electrochemical monitoring and/or measuring the concentration and/or constitution of a sample solution. The present invention has particular utility in connection with liquid chromatography and will be described in connection with such use.

Liquid chromatography is a well-known analytical technique in which a sample material is separated into its component species by dissolving the sample material in a carrier fluid to form a mobile phase which is then passed continuously through a solid phase. Generally the solid phase comprises a bed of ion exchange resins in powder or bead form, arranged in a stack or column. The various species contained in the sample material separate as a result of their different values of attraction for the various ion exchange resins in the bed to produce a so-called eluant solution which is then passed through a detection device. Classically, detection devices for liquid chromatography have been based on measurements of optical phenomena such as differences in indices of refraction or ultraviolet absorption of the various species in the chromatographic eluant.

Two prerequisites for commercial chromatography systems are: (1) sharp separation by the solid phase of the various species in the sample so that individual species will appear at different times in the eluant, i.e. the sample is resolved into its component species; and (2) convenient means of continuously and accurately detecting and analyzing the separated species in the eluant. At the current state of the art chromatographic separation generally can be achieved at a level of selectivity that is substantially more precise than the level of sensitivity of detection achieveable using classical optically based detection devices. More recently, detection devices based on electrochemical measurements have been proposed for use in connection with liquid chromatography separations. One such proposed electrochemical detection device employs a hanging drop mercury electrode suspended in the eluant solution. However, as noted in U.S. Pat. No. 3,706,381, detectors employing hanging drop mercury electrodes have not proved to be entirely satisfactory due to the considerable noise associated with the dropping mercury. It has also been proposed to employ solid electrodes for directly measuring species in an eluant solution. One such proposed device employs a test electrode in the form of a solid graphite button or a carbon or graphite paste flat plate for contacting the eluant stream from a liquid chromatography column. However, electrochemical detection devices of this type generally are able to achieve sensitivity of 100 picograms at best, and may suffer from decay of sensitivity. Also, while electrochemical detection devices employing carbon or graphite paste electrodes may function well for many applications of reverse-phase chromatography, problems can develop when nonaqueous solvents are used due to the combination of a high volume flow rate with the mechanical instability of the carbon paste matrix. In addition, the relatively high electrical resistance of nonaqueous mobile phases can limit the linear range (on the high end) of thin layer amperometric detectors due to ohmic potential losses along the thin-layer channel. Another disadvantage of known electrochemical detection devices is that such devices generally rely on measuring changes in charge transfer phenomena; thus known electrochemical detection devices generally are limited in use to detecting only those materials capable of undergoing charge transfer.

It is thus a primary object of the present invention to provide a novel and improved electrochemical detection system, i.e. method and apparatus, which overcomes the aforesaid and other problems and limitations of the prior art.

Another primary object is to provide a novel and improved electrochemical detection apparatus for use in combination with a chromatographic separation apparatus.

Another more specific object is to provide a novel and improved electrochemical detection apparatus for analyzing the eluant stream from a liquid chromatographic separation.

In order to effect the foregoing and other objects there is provided an electrochemical detection apparatus comprising a flow-cell having at least one active testing electrode, at least one reference electrode, and at least one counter electrode. Each electrode comprises a liquid impervious solid body having a bore extending therethrough with the electrode active surface located in the bore. The electrodes are arranged in a stack, electrically insulated from one another with their respective bores aligned so as to define a flow channel through which liquid to be detected can be passed. In a preferred embodiment of the invention at least one of the reference electrodes is actively driven to supply a stable reference potential against which other electrochemical responses can be measured. Various electrochemical responses are achieved by varying the construction, number and arrangement of electrodes in the stack, and the potentials applied to the electrodes.

Yet other objects of the invention will in part appear obvious and will in part appear hereinafter. The invention accordingly and comprises the apparatus processing the construction, combination of elements, and arrangement of parts, and the processes comprising the several steps and relation of one or more of such steps with respect to each of the others, all of which are exemplified in the following detailed description, and the scope of the application as will be indicated in the claims.

For a fuller understanding of the nature and objects of the present invention reference should be had to the following detailed description taken in connection with the accompanying drawings wherein:

FIG. 10 is a top plan view, in cross section, of one form of electrode suitable for use as a reference electrode in the electrochemical detection cell of FIG. 2;

The present invention provides an electrochemical detection apparatus capable of responding not only to charge transfer phenomena of species in a sample solution, but also to the capacitance of the so-called electrode double layer of the sample solution. As applied to liquid chromotography, the sample solution comprises chromatographic eluant. Electrochemical measuring of changes of the electrode double layer has been described by Pretorious and Hann in their U.S. Pat. No. 3,649,498, issued Mar. 14, 1972. Pretorious and Hann report that is is possible to identify changes in the electrode double layer on a detection electrode produced by the so-called "Zeta Effect". According to Pretorious and Hann when a liquid is in contact with a surface, e.g. the solid wall of a tube, a so-called "Zeta Potential" arises across the interface between the solid wall and the liquid. Any flow of liquid relative to the surface will be the result of the development of a streaming potential between opposite ends of the interface, e.g. between opposite ends of the tube through which the liquid is flowed. Moreover, the Zeta Potential increases with flow velocity, and is very sensitive to the composition of the liquid, both with regard to ingredients and their respective concentrations. The present invention permits detection and measurement of charge transfer phenomena and/or changes in the electrode double layer of a sample solution.

Further understanding of the features and advantages of the present invention will be had from the following detailed description of the invention which illustrates a preferred form of electrochemical detection apparatus of the present invention in combination with a liquid chromatography separation apparatus. It will be understood, however, that the electrochemical detection device of the present invention may be advantageously employed for detecting the presence of and measuring the concentration of sample solutions from a variety of sources.

Figure 1:
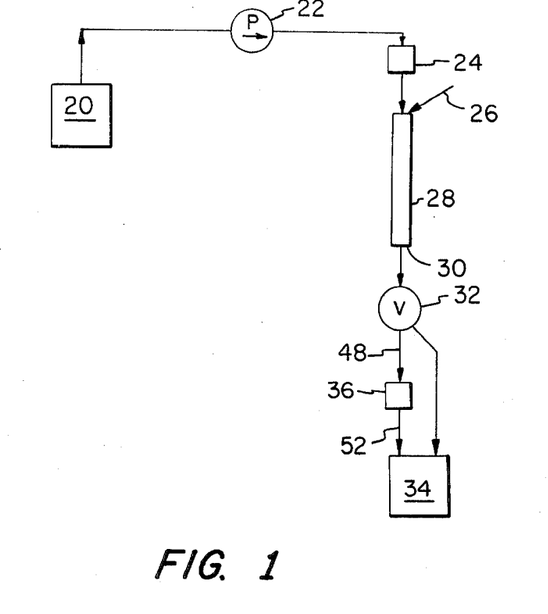
FIG. 1 is a schematic view of one form of liquid chromatography apparatus incorporating an electrochemical detection apparatus in accordance with the present invention.

Referring to FIG. 1, there is illustrated a liquid chromatography apparatus and electrochemical detection apparatus in accordance with the present invention. The illustrated liquid chromatography apparatus includes a mobile phase reservoir 20 coupled through a constant volume pump means 22 and an injection valve 24 and sample inlet 26 to the top of a liquid chromatography column indicated generally at 28. In practice, sample materials to be tested are introduced into the chromatography apparatus either by direct injection of microliter amounts of sample material into the chromatography column 28, e.g. through a syringe at sample inlet 26, or the sample material may be introduced into the chromatography column 28 as a dilute solution of sample material at injection valve 24. Thus, if desired, either injection valve 24 or sample inlet 26 may be omitted from the system. Chromatography column 28 is packed with selected ion exchange resins in bed or powder form. The selection of the mobile phase, and the selection and packing order of the ion exchange resins will depend on the particular separations desired and can readily be determined by one skilled in the art and thus will not be further described herein. The base of chromatography column 28 is coupled via an outlet 30 to a splitter valve 32 which divides the eluant from the chromatography column 28 between a sample collection vessel or waste container 34 and an electrochemical detection apparatus made in accordance with the present invention, and indicated generally at 36.

The illustrated chromatography apparatus (other than the electrochemical detection apparatus 36) is conventional and may be of the type described by P. H. Freeman and W. L. Zielinski, in U.S. bureau of Standards Technological Note Number 589, Page 1, (July 1970 to June 1971). Moreover, it should also be noted that the electrochemical detection apparatus 36 of the present invention is not limited to use with the particular type of chromatography apparatus illustrated in FIG. 1, which is merely given as exemplary.

As mentioned supra, a problem and disadvantage of prior art electrochemical detection devices is their limited sensitivity in dilute solutions. Thus, despite advances that have been made in chromatography column technology such as high pressure liquid chromatography which permits resolution of a sample solution into its respective components in the nannogram range, a limitation to commercial development and use of liquid chromatography in high resolution applications has been the lack of detection devices capable of detecting such minute quantities. Generally, the requirements of electrochemical detection devices capable of discriminating minute quantities in solution are (1) high electrode sensitivity, (2) ultra-low cell volume, (3) ultra-high electrode active area to sample volume, (4) wide range of electrode response (5) large linear range of response, (6) reproduceability under varying experimental parameters such as temperature and flow rate, and (7) long term stability and reliability. These requirements are met, in part, by the unique construction of the electrochemical detection apparatus 36 of the present invention Referring to FIGS. 2 and 3, electrochemical detection apparatus 36 comprises an electrochemical detection cell indicated generally at 38 and including a holder assembly having a pair of end plates 40 and 42 respectively. In one embodiment shown in FIGS. 2 and 3 end plates 40 and 42 comprise short, generally cylindrical plates formed of a rigid, liquid impervious, electrically insulating, chemically inert material such as a synthetic polymeric material, e.g. a ceramic, an unplasticized polyvinyl chloride, a polytetrafluoroethylene fluorocarbon resin, or the like. Formed integrally on the inside wall of end plate 40 is a flat hub 44. An internally threaded screw mounting 46 is formed in the outside wall of plate 40 for connecting the electrochemical detection cell 38 to the outlet 30 from chromatography column 28 via splitter valve 32 and a liquid conduit 48. In similar manner an integral hub 48 is formed on the inside wall of end plate 42, and an internally threaded screw mounting 50 is formed on the outside wall of plate 42 for connecting the outlet from electrochemical detection cell 38 via conduit 52 to liquid waste container 32. An inlet passageway 56 adopted to receive an eluant flow stream from chromatography column 28 is formed through end plate 40, and an outlet passageway 58 adopted for withdrawing eluant from electrochemical cell 38 is formed through end plate 42.

Figure 2:
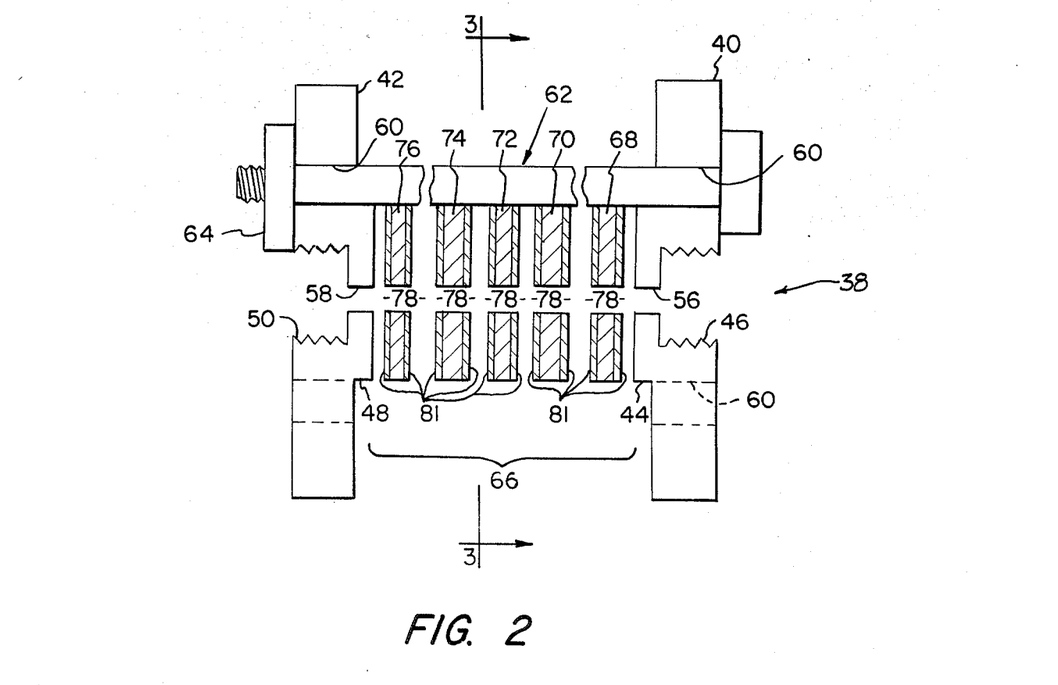
FIG. 2 is an exploded front elevational view, partly in section, showing details of a preferred form of electrochemical detection cell portion of the apparatus of FIG. 1.
Figure 3:
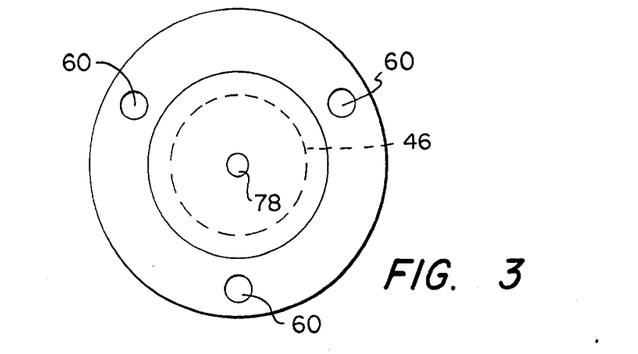
FIG. 3 is a cross sectional view of the electrochemical detection cell of FIG. 2, taken along lines 3—3.

A plurality of bolt holes 60 are formed through the end plates 40 and 42 and provide entry for bolts, only one of which 62 is shown. As will become clear from the description following, bolts 62 align the individual electrodes of electrochemical detection cell 38 and, when anchored with nuts 64, apply pressure to keep the electrochemical detection cell 38 together.

As mentioned supra, for detecting minute quantities in solution an electrochemical detector should have an ultra-low cell volume and an ultra-high electrode active surface area to sample volume. The instant invention satisfies these and other requirements, in part, by providing electrochemical detection cell 38 with a plurality of electrically discrete electrode elements assembled in a stack 66, and restricting the cell working volume to a small bore extending through the stack. For purposes of illustration stack 66 is shown as comprising five electrically discrete electrode elements 68, 70, 72, 74 and 76 arranged as follows:—Two active testing electrodes 68 and 72, two reference electrodes 70 and 74, and a counter electrode 76. As will become clear from the description following, stack 66 may comprise more than five electrodes, or the stack may comprise as few as three electrically discrete electrode elements, i.e. a single active testing electrode, a single reference electrode, and a single counter electrode.

Referring also to FIGS. 4 to 13, each electrode element comprises a generally flat cylindrical disk. All the disks have the same approximate diameter, and generally, but not necessarily, the same approximate thickness. One, or a plurality of holes or passageways 78 are formed through each electrode element, and passageways 78 are located so that when the disks are assembled in the stack 66 the passageways 78 are aligned so as to define one, or a plurality of fluid flow channels through the detection cell 38 between the cell inlet passageway 56 and the cell outlet passageway 58. The individual electrode elements 68, 70, 72, 74 and 76 are electrically insulated from one another in stack 66 by means of a thin, coating of suitable electrically insulating material 81 on each or selected ones of the electrode elements. Alternatively, the individual electrode elements in the stack 66 may be electrically insulated from one another by means of thin, flat spacers (not shown) of an electrically insulating material such as a synthetic polymer material. Coating 81 or the spacers, as the case may be, should also be provided with apertures or passageways aligned with the electrode passageways 78. As will become clear from the description following, passageways 78 substantially comprise the cell entire working volume. Thus, by limiting the size of passageways 78 the cell working volume can be made to be quite small.

As mentioned supra, the electrode active areas are located in passageways 78. Typically the active testing electrodes (68 and 72) and the counter electrode or electrodes (76) are of similar construction. Generally these electrodes comprise disks of suitable electrode base material such as graphite, pyrolytic graphite or platinum, and the electrode active surface areas comprise the disks interior wall surface areas defining passageways 78. Alternatively, the active testing electrodes and counter electrodes may comprise disks of chemically inert, electrically insulating material such as a synthetic polymeric plastic, and having coatings of active electrode material such as mercury, gold, silver, bismuth, $PbO_2$, $MnO_2$ or other suitable electrode material. The electrode material may be deposited on the insulating disks surface areas at least in part defining passageways 78 using known techniques such as electrochemical deposition. Graphite or other chemically inert, electrically conductive material also may be used as the substrate material for carrying the coatings of active electrode material. As will become clear from the description following, forming the electrode active surface areas on the surface areas defining passageways 78 maximizes the electrode active area for a given cell volume. Also, keeping passageways 78 small minimizes the electrode double-layer and the response time of the electrodes, and maximizes mass transfer of sample solution to the electrode active surfaces. If desired, a plug of porous electrode base material, e.g. a graphite plug, may be mounted in passageways 78 to increase the effective active surface area of the electrodes as will be described in detail hereinafter.

Figure 4:
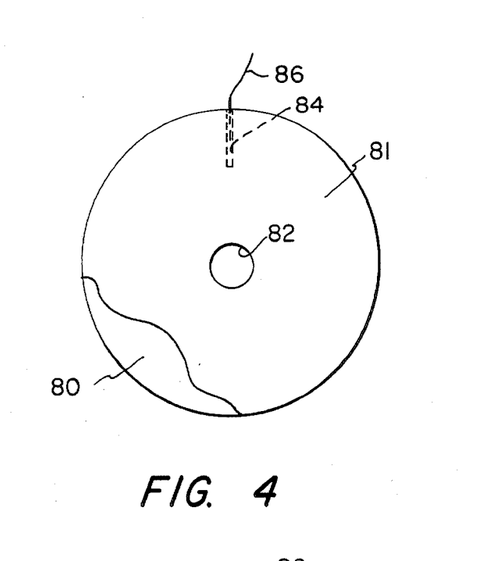
FIG. 4 is a top plan view, in cross section, of one form of electrode suitable for use as an active testing electrode and/or as a counter electrode in the electrochemical detection cell of FIG. 2.
Figure 5:
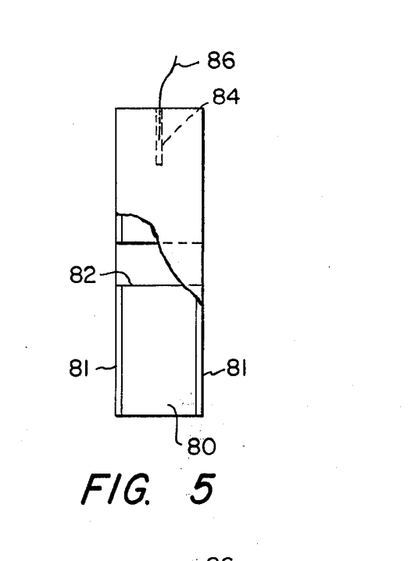
FIG. 5 is a side elevational view, in cross section, of the electrode of FIG. 4.

FIGS. 4 and 5 illustrate a specific form of electrode element suitable for use as active testing electrodes (68 or 72), and/or as a counter electrode (76) in the electrochemical detection cell of the present invention. The illustrated electrode element comprises a flat cylindrical disk 80, 0.500 inch in diameter by 0.040 inch thick. Disk 80 is formed of an electrode base material such as a metal or graphite. Disk 80 is coated with a thin (e.g. 0.002 inch thick) coating 81 of an electrically insulating material such as Teflon FEP (Teflon FEP is a registered trademark of the E. I. Dupont de Nemours Company for a synthetic tetrafluorohydrocarbon). A 0.013 inch diameter through-hole or passageway 82 is provided on center through disk 80 (and coating 81). As described supra the electrode active surface area is thus defined by the internal wall area 83 of disk 80 which subtends passageways 82. Electrical contact to the electrode active surface area (i.e. internal wall area 83) is provided by drilling a 0.015 inch deep by 0.0120 inch blind hole 84 in the rim of disk 80, and fixing a 24 AWG stranded wire 86 in the hole 84, for example, by means of an electrically conductive adhesive. Various electrically conductive adhesives are known in the art and are available commercially. Typically, such adhesives comprise an epoxy containing particles of conductive material such as graphite or a noble metal, such as silver. Further details regarding the selection of the conductive adhesive are believed unnecessary to an understanding of the present invention.

Figure 6:
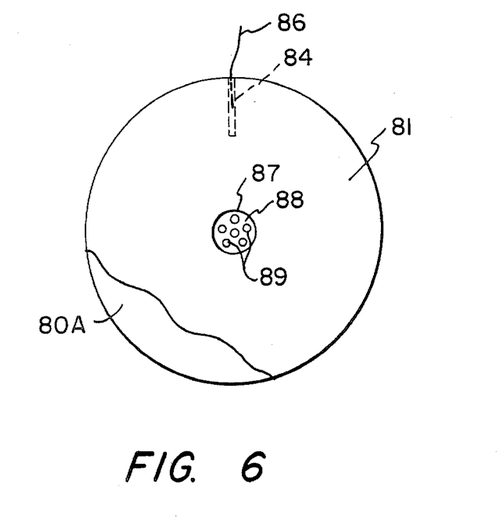
FIG. 6 is a top plan view, in cross section, of an alternative form of electrode suitable for use as an active testing electrode and/or as a counter electrode in the electrochemical detection cell of FIG. 2.
Figure 7:
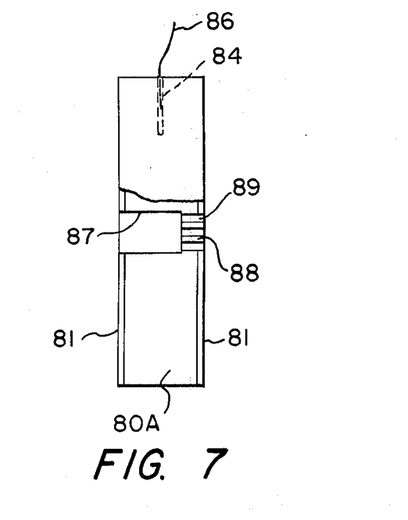
FIG. 7 is a side elevational view, in cross section, of the electrode of FIG. 6.

The active testing electrodes (68 or 72) and/or the counter electrode (76) in electrochemical detection cell 38 may take other forms. Thus, as shown in FIGS. 6 and 7, the electrode active surface area may be increased relative to the passageways 82 size by milling the disk 80 to a depth of 0.005 inch on center to form a 0.060 inch diameter hole 87, but leaving a thin membrane 88 of electrode material, and milling a plurality, e.g. six 0.013 inch holes in a close packing pattern through membrane 88. One skilled in the art will recognize that the electrode element shown in FIGS. 6 and 7 has a greater active surface area for a given passageway 82 size than the electrode element illustrated in FIGS. 4 and 5, and thus may have a greater sensitivity.

Figure 8:
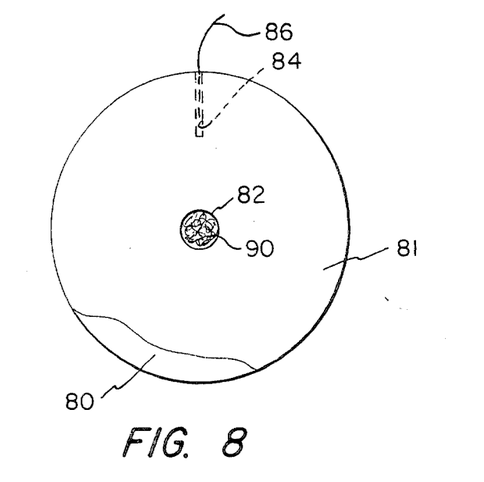
FIG. 8 is a top plan view, in cross section, of still another form of electrode suitable for use as an active testing electrode and/or as a counter electrode in the electrochemical detection cell of FIG. 2.
Figure 9:
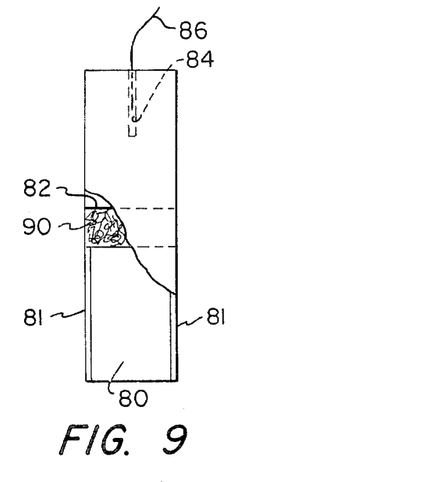
FIG. 9 is a side elevational view, in cross section, of the electrode of FIG. 8.

Still another form of electrode element suitable for use as an active testing electrode (68 or 70), and/or as a counter electrode (76) in the electrochemical detection cell 38 of the present invention is shown in FIGS. 8 and 9. The FIGS. 8 and 9 embodiment is similar to that shown in FIGS. 4 and 5, but also includes a flow restrictor 90 in the form of a fiber form plug formed of active electrode material such as graphite in the through-hole or passageway 82. Alternatively, flow restrictor 90 may comprise a solid porous plug of active electrode material such as Type A 708 Poco Graphite (the latter is available commercially from Union 76 Oil Co.). If desired, the flow restrictor 90 may be formed in the shape of a truncated tetrahedron, and positioned in passageway 82 with the sharp point facing the direction of flow. Flow restrictor 90 may be cemented in position by a thin film of electrically conductive cement such as graphite epoxy, or the flow restrictor may be held in position by liquid flow pressure. One skilled in the art will recognize that the electrode element shown in FIGS. 8 and 9 has a greater active surface area for a given passageway 82 size as compared to the electrode element shown in FIGS. 4 and 5 and FIGS. 6 and 7 and thus may have a greater sensitivity.

Figure 11:
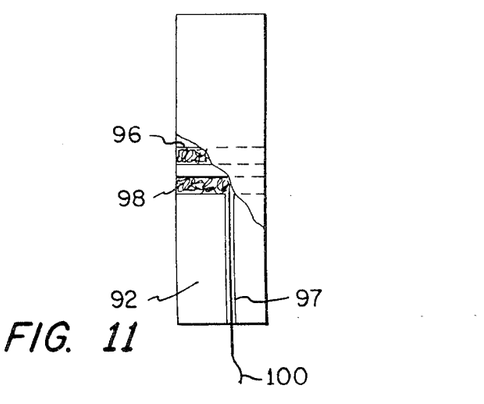
FIG. 11 is a side elevational view, in cross section, of the electrode of FIG. 10.

FIGS. 10 and 11 illustrate one form of electrode element suitable for use as a reference electrode (70 or 74) in the electrochemical detection cell 38 of the present invention. As is well known in the art, a reference electrode supplies a stable reference potential against which other electrochemical reactions can be measured. The reference electrode illustrated in FIGS. 10 and 11 comprises a 0.180 inch thick by 0.500 inch diameter disk 92 formed of an electrically insulating material such as Teflon. A 0.170 inch diameter hole or passageway 96 is drilled on center through the disk 92, and the hole 96 is filled with a salt bridge medium such as a porous Vycor plug 98. A 0.020 inch diameter hole or passageway 99 is drilled on center through the center of the porous Vycor plug 98. Electrical contact to porous Vycor plug 98 is made by providing a 0.0120 inch drilling 97 in the rim of disk 92 through to hole 96, and running a silver/silver chloride wire 100, (0.1 NaCl) in drilling 97.

Figure 12:
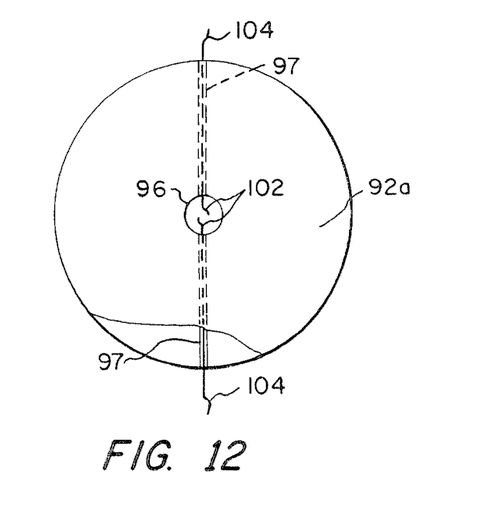
FIG. 12 is a top plan view, in cross section, of an alternative form of electrode suitable for use as a reference electrode in the electrochemical detection cell of FIG. 2.
Figure 13:
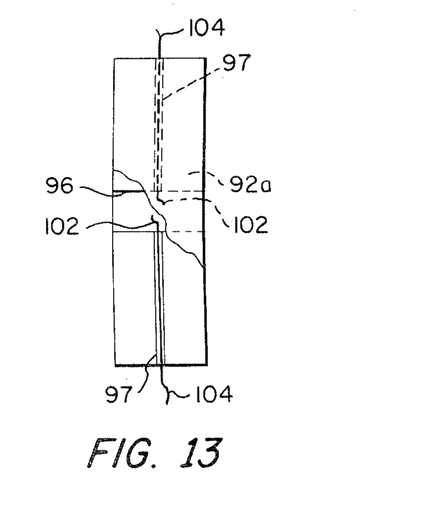
FIG. 13 is a side elevational view, in cross section, of the electrode of FIG. 12.

The reference electrodes may take other forms. One alternative and advantageous form of reference electrode is shown in FIGS. 12 and 13. As in the reference electrode shown in FIGS. 10 and 11, the reference electrode is carried on a Teflon disk 92a. The latter is similar to the Teflon disk 92 shown in FIGS. 10 and 11. However, in the FIGS. 12 and 13 embodiment passageway 96 comprises a 0.020 in. diameter hole, and the salt-bridge reference (Vycor plug 98) is substituted by an inert metal reference terminal such as one or a plurality of palladium or platinum wires 102. Alternatively, the wall surfaces defining passageway 96 may be plated with inert metal or covered with an inert metal foil to provide the metal reference terminal. As will be described in detail hereinafter, reference electrodes of the FIGS. 12 and 13 type are actively driven electrically to provide a reference voltage. Electrical contact to the inert metal reference terminal is made via a palladium or platinum wire 104, respectively, in drilling 97. An advantage of the FIGS. 12 and 13 reference electrode is the elimination of solution leakage and solution maintenance problems generally associated with conventional, i.e. salt-bridge based reference electrodes. Also, in the FIGS. 12 and 13 electrode structure the reference terminals can be formed of one or more micro wires, which permits greater flexibility in the design of the electrochemical detection cell.

Figure 17:
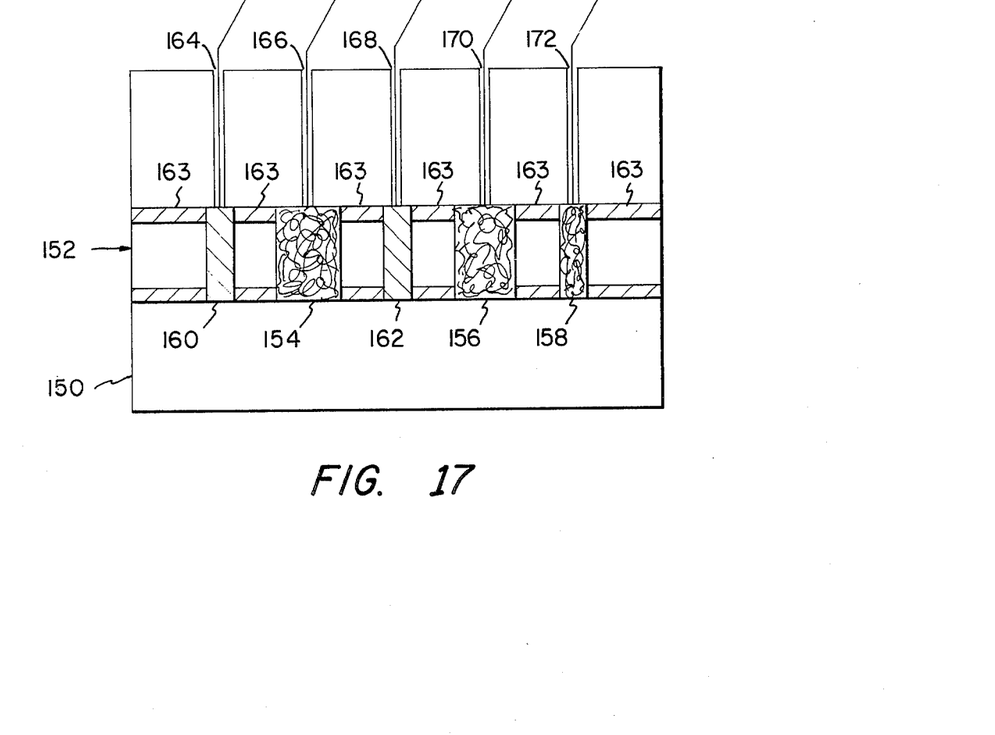
FIGS. 17 and 18 are side elevational views, in cross section, of alternative forms of electrochemical detection cells made in accordance with the present invention.
Figure 18:
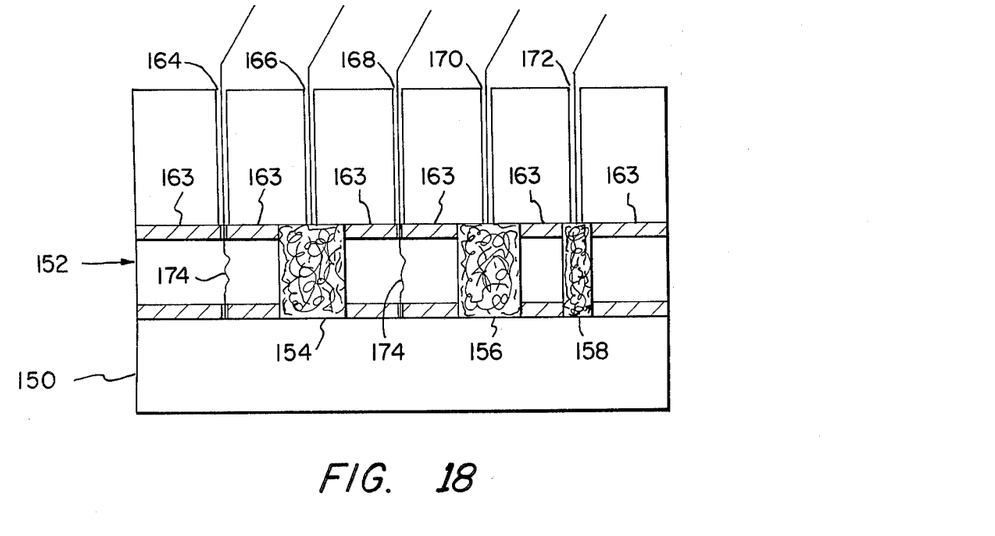

The electrochemical detection cell may take other forms. For example, as shown in FIGS. 17 and 18 the holder assembly may comprise a solid body 150 of electrically insulating material such as a synthetic polymeric material such as Teflon, Kel-F, Halar, Fluoron, polypropylene or other commercially avaiable polymeric material, and having the individual electrode elements arranged in a stack in spaced relation to one another in a bore 152 which extends through the body 150. Referring in particular to FIG. 17, the body 150 comprises a solid block of Teflon and bore 152 comprises a round through-hole or passageway of 0.040 inch diameter. A plurality of discrete electrode elements, e.g. five electrodes including a pair of active test electrodes 154,156 and a counter electrode 158 in the form of 0.040 inch diameter by 0.040 inch thick porous graphite cylindrical plugs, and a pair of reference electrodes 160, 162 in the form of 0.040 inch diameter by 0.040 inch thick porous Vycor cylindrical plugs, are arranged in a stack in bore 152. The various electrode elements are separated from one another in the stack by short pieces of Teflon tubing spaces 163. Alternatively, spacers 163 may comprise porous Teflon wafers. Electrical connection to active testing electrodes 154, 156, counter electrode 158, and reference electrodes 160, 162 is made by providing 0.0120 inch drillings 164 to 172 in the rim of body 150 through to bore 152, and running suitable electrically conductive wires in the drillings, (for example 24 AGW stranded wires for the active testing electrodes, and the counter electrode, and silver/silver chloride wires for the reference electrodes). Alternatively, as shown in FIG. 18, the reference electrodes 160, 162 may comprise inert metal reference terminals such as one or a plurality of palladium, palladium oxide or platinum wires 174, and the counter electrode may comprise one or a plurality of noble metal wires such as platinum.

The electrochemical detection cells shown in FIGS. 17 and 18 preferably comprise a Teflon body 150, and are assembled by first heating the Teflon body 150 to elevated temperature, e.g. 200° to 300° C., whereupon the Teflon body 150 expands. This facilitates loading the electrode elements and spacers into bore 152, and the wires into drillings 164 to 172. Upon cooling to ambient temperature the Teflon body 150 contracts to its original size, whereby to grip and tightly seal around the electrode elements, spacers and wires.

Alternatively, the electrode elements, spacers and wires may be assembled in a jig, and the assembly potted with a suitable material such as a synthetic polymer. Obviously, care must be taken to protect the electrode pores, e.g. the electrodes may be wax impregnated prior to potting, or the bores may be protected with a wire which can be pulled following potting.

Figure 14:
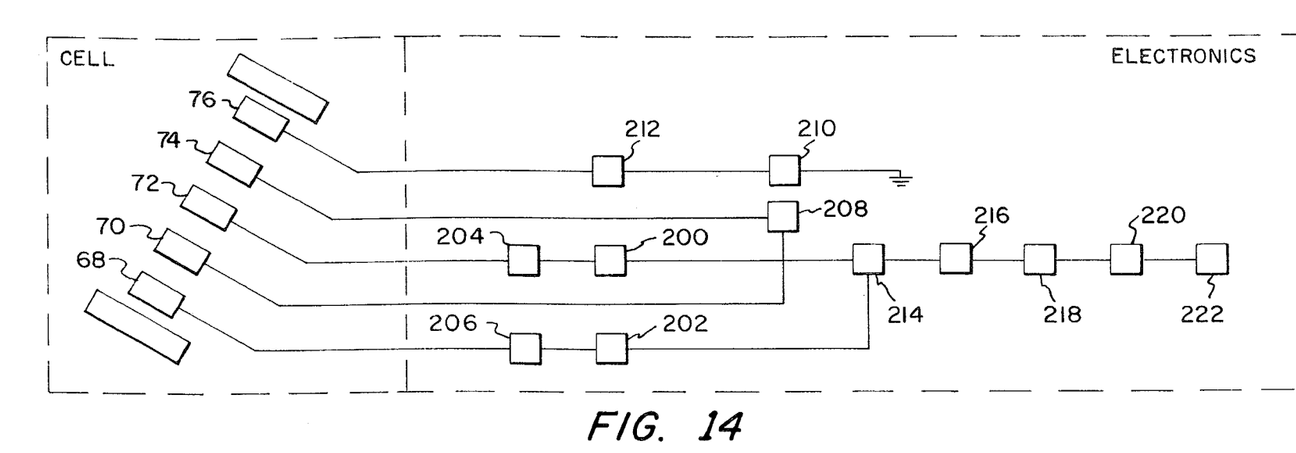
FIGS. 14 and 15 are block diagrams of the electrical controls and functions of the electrochemical detection apparatus of FIG. 1.

Completing electrochemical detection cell 38 are electrical controls and circuits for connecting the active testing electrode elements (68 and 72) to controlled testing potentials; electrical controls and circuits for connecting the reference electrode elements (70 and 74) to a reference potential; and, electrical controls and circuits for connecting the remaining electrode element (76) to a working potential, or to ground. These electrical controls and circuits are illustrated diagramatically in FIGS. 14 and 15. Referring to FIG. 14 the electrical controls and circuits include an individual current amplifiers 200,202 and potential offset controls 204,206 for applying selected electrical potentials to each of the active testing electrodes 68 and 72, respectively; a constant current source indicated generally at 208 for applying a constant reference potential to the two reference electrodes 70 and 74; and a third current amplifier 210 and potential offset control 212 for applying a working potential to counter-electrode 76, i.e. so as to provide a source of current to the cell. Alternatively, as noted infra, counterelectrode 76 may be held at ground. The current or signals from first and second active testing electrodes 68 and 72 are fed to a logic module in which the currents or signals may be manipulated, e.g. added or subtracted, and, if desired, multiplied for calibration purposes. By way of example, the current or signals from the two active electrode segments in cell 38 can be fed to a current convertor subtractor 214 with two variable gains for adjustment. The resulting signal is then fed to a signal accumulator 216, and then to a calibration blanking circuit 218 which also may have a variable gain or calibrator 220. The signal from the calibration blanking circuit 218 is then fed to a strip recorder or single or multichannel readout 222 of conventional construction.

Figure 15:
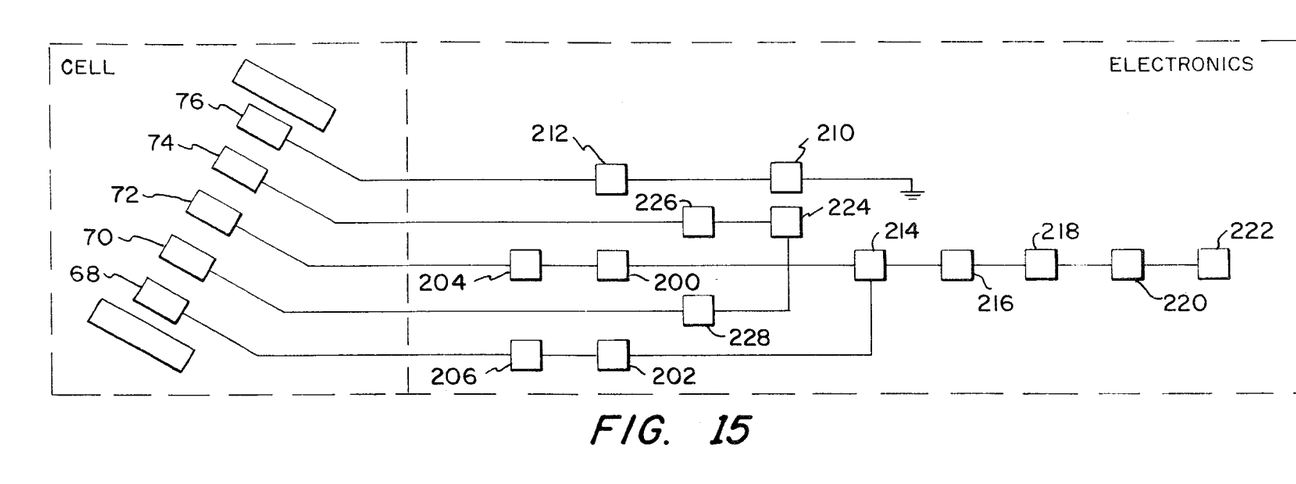

Alternatively, as shown in FIG. 15 the electrical controls and circuits may comprise, in place of the constant current source 208, an impedance network indicated generally at 224, coupled in feedback arrangement to a pair of follower amplifiers 226,228 whereby the reference electrodes 70 and 74 may be actively driven in response to changes in test solution. As a result a constant potential can always be maintained between each reference electrode and the test solution. Actively driving the reference electrodes in response to changes in the testing solution is believed unique and, has the advantage of minimizing IR drops and cell volume, and also avoids the maintenance problems and leakage problems associated with conventional salt-bridge based reference electrodes.

Depending on the number of electrode elements included in the detection cell, and the arrangement, i.e. stacking order of the individual electrode elements, a number of operating modes are possible and provide various advantages as will be described in detail hereinafter. By way of example, but not limitation for an electrochemical detector made in accordance with FIGS. 2 and 3 and comprising two active testing electrodes 68 and 72, two reference electrodes 70 and 74, and a single counter electrode 76, the following operating modes are possible:

(1) A single active testing electrode at a controlled testing potential, with a single channel readout;

(2) Two active testing electrodes, each at a different testing potential, with two channel readouts;

(3) Two active testing electrodes, each at a different testing potential, with a single differential readout;

(4) Two active testing electrodes, at similar controlled testing potentials, with a single differential readout; and (5) One active testing electrode at a potential below the wave of interest, the other active testing electrode at a controlled testing potential, and a single channel readout responsive only to the electrode at the controlled testing potential.

Further understanding of the principles and advantages of the present invention may be had by reference to the following examples which illustrate the use of the electrochemical detection device in accordance with the present invention.

EXAMPLE I

An electrochemical detection cell made in accordance with FIGS. 2 and 3 was used. The cell comprised two active testing electrodes (68 and 72) and a counter electrode (76) of the FIGS. 4 and 5 type, and two reference electrodes (76, 74) of the FIGS. 10 and 11 Vicor salt-bridge Ag/Ag Cl type. Each electrode comprised a flat disk approximately 0.060 inch in diameter by 0.020 inch thick. The active testing electrodes and the counter electrode were comprised of graphite bodies with $0.8\mu$ pore size 50% porosity, coated with a 0.002 inch thick coating of Teflon FEP (available from E. I. DuPont de Nemours and Co.). A single 0.013 inch diameter through hole 78 was provided on center, of each electrode.

The basic procedure was to dissolve small amounts of epinephrin, norepinephrin and methyl-L-dopa in Methyl Alcohol to form a sample solution. The sample solution was then introduced into a Model 848 liquid chromatography system (available from E. I. DuPont de Nemours and Co.). The chromatography column was packed with a Zorbax- C-8 column packing from E. I. DuPont De Nemours and Co. (The manufacturer describes the packing as comprising an eight-carbon hydrocarbon on an inert carrier). Flow rate through the chromatography column was 1.5 ml/min. The eluant from the chromatography column was run sequentially through the conventional optically based detection apparatus of the Model 848 liquid chromatography system, and then through the electrochemical detection apparatus made in accordance with the present invention. The electrical signal outputs from the conventional, i.e. optically based detector apparatus, and from the electrochemical detection apparatus in accordance with the present invention were recorded on the automatic recorder and shown respectively in FIG. 16 as a solid line (for the optically based apparatus), and as a broken line (for the electrochemical detection apparatus).

Figure 16:
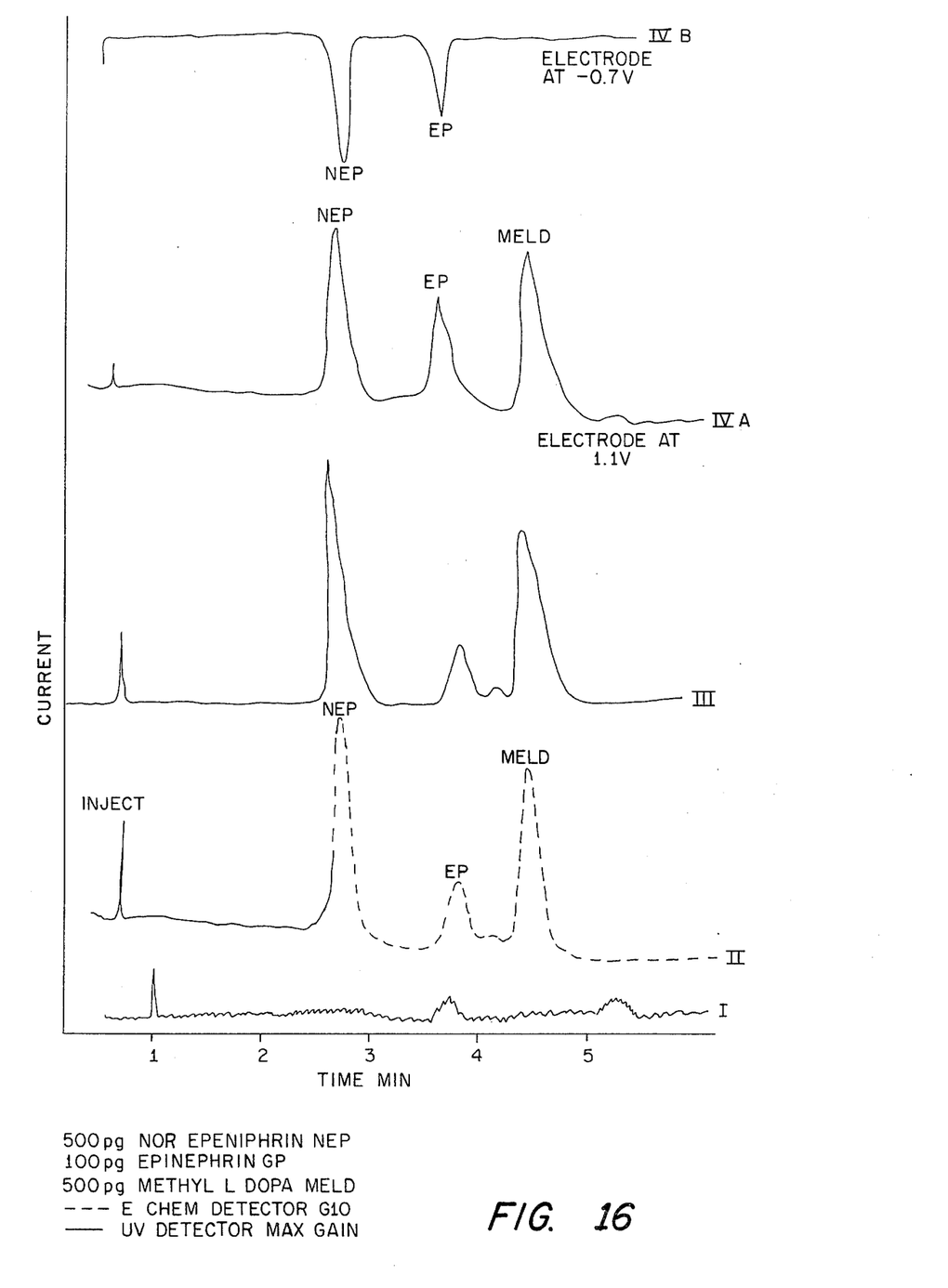
FIG. 16 is a series of chart recordings show measurements made on the eluant from a liquid chromatography apparatus employing an electrochemical detection apparatus made in accordance with the present invention, and measurements made on the same eluant using a conventional optically based detection apparatus, and illustrating the advantages of the electrochemical detection apparatus of the present invention.

In order to illustrate the simplest mode of operation one of the testing electrodes 68 was set at a potential of 0.7 V. vs. the standard Vycor salt-bridge Ag/Ag Cl reference electrode 70, i.e. below the wave of interest so as to not pick up any signal, while the other active testing electrode 72 was set at a testing potential of 1.1 V. relative to the standard Vycor salt-bridge Ag/Ag Cl reference electrode. The counter electrode 76 was driven on demand to supply current to the cell. Electrochemical reactions of the chromatographic eluant were sensed by active testing electrodes 68 and 72, and the resulting signals are fed to a logic module which differentiated the signals and applied a multiple for calibration purposes. The calibrated signal was then fed to a strip recorder, and was recorded in FIG. 16, line II. As can be seen in FIG. 16, the electrochemical detection apparatus of the present invention provides a signal which detects the epinephrin and the norepinephrin present in the eluant, while the same compounds are not seen at all by the conventional optically based detection apparatus (FIG. 16, line I).

The extreme sensitivity of the electrochemical detection apparatus made in accordance with the present invention as demonstrated in Example I can be explained by the following:

As is well known the equation governing Faradic reactions is defined by:

$$i = nFAD\frac{C}{\delta}$$

Where:
F is the Faraday (96500 Coulombs);
c is the current from the reaction in amps;
n is the number of electrons per unit of species;
A is the area of the electrode in cm$^2$;
C is the concentration of the Species in moles/cm$^3$; and
$\delta$ is the unstirred layer next to the electrode in cm.

Now, the electrochemical detection cell 38 constructed as described in this Example I has an approximate working volume V of 0.4 $\mu$l ($4\times 10^{-5}$ cm$^3$), and testing electrode active surface area of approximately 4.2 cm$^2$. Assuming typical values of n=1, D=$10^{-5}$ cm$^2$/sec., $\delta$ is a maximum of 0.4$\mu$ or $4\times 10^{-5}$ cm from the pore size of the filter 0.8$\mu$.

For a substance of molecular weight 100, 1 ng/cm$^3$ = $10^{-11}$ moles/cm$^3$.

Then, for 1 ng/cm$^3$.

$$i = 1 \times .965 \times 10^5 \times \frac{4.2 \times 10^{-5} \times 10^{-11}}{4 \times 10^{-5}}$$

i=1.10$\times 10^{-6}$a or 1.10 $\mu$a.

Typically, a graphite type electrode will give an inherent electrode background of plus/minus 1 to 5 $\mu$a/cm$^2$. Thus a detection cell made in accordance with the foregoing will be working at a 10% signal over non-Faradic background noise at the nanogram level. Obviously, any Faradic background noise would contribute to the signal depending on the concentration of the reacting species.

However by differentiating the signals from electrode 68 and 72 (where one electrode is at 0.7 V. vs. the Vycor salt-bridge Ag/Ag Cl, i.e. in a region of no Faradaic reaction), the background of approximately +1 to 5 $\mu$a/cm$^2$ is nulled out. Also long and short term drift in the background is nulled out.

EXAMPLE II

Example I was repeated with the following change:—Active testing electrode 68 was fixed at a potential of 1.1 V. vs. the standard Vycor salt-bridge Ag/Ag Cl reference electrode 70, and active testing electrode 72 was also fixed at a potential of +1.1 V. vs. the standard Vycor salt-bridge Ag/Ag/Cl reference electrode 74. Also for this Example II, both active testing electrodes were made somewhat thicker in cross-section so as to increase their respective active electrode areas. As before, counter electrode 76 was driven on demand to supply current to the cell 38. The current or signals from active testing electrodes 68 and 72 were then fed to a logic module wherein one signal was subtracted from the other and a multiple applied for calibration purposes. One skilled in the art will recognize that setting the two active test electrodes at identical potentials, i.e. in accordance with this Example II, absolutely nulls Faradaic and solution background. Thus, to obtain a signal representative substantially only of the reaction of interest, this mode of operation relies on effectively completing the electrochemical reaction to 99%, or more on the first active testing electrode in the stack, i.e. the upstream electrode 68.

That all species present in the solution and capable of undergoing charge transfer at the applied potentials can be expected to go virtually to complete electrochemical reaction can be seen from the following:—As is well known in the art the cell time constant (k) for a continuously flowing stream can be approximated by:

$$K = e\frac{V\delta}{AD}$$

Where
e = the base of Naperian logantham 2.7
V = the cell volume
$\delta$ = is the Nernst layer (0.4$\times 10^{-4}$ cm fixed by electrode porosity)
A = is the electrode area, and
D = is the diffusion constant Thus, for a detection cell 38 constructed as shown in FIGS. 2 and 3, and having an approximate volume V of 4 $\mu$l ($4\times 10^{-4}$ cm$^3$) and a diffusion constant of $10^{-5}$ cm$^2$/sec., the cell time constant K is:

$$K = \frac{2.7 \times 4 \times 10^{-4} \times 0.4 \times 10^{-4}}{4.2 \times 10^{-5}}$$

K = $10^{-5}$ sec.

Thus for 1 cm$^3$/min. flow rate the residence time in the electrochemical detection cell (cell volume $4\times 10^{-4}$ cm$^3$) is:

$$\frac{4 \times 10^{-4} \text{cm}^3}{1/60 \text{ cm}^3/\text{sec}} = 24 \times 10^{-5} \text{sec.}$$

or approximately 2400 cell constants which assures virtual complete electrochemical reaction of any electroactive species (i.e. at the applied potentials) flowing through the cell.

The result is shown as line III in FIG. 16.

EXAMPLE III

Example II is duplicated with the following changes—The standard Vycor salt-bridge reference electrodes were substituted by inert metal (platinum) reference terminal of the FIGS. 12 and 13 type. Active testing electrode 68 was fixed at a potential of +1.1 V. vs. reference electrode 70, active testing electrode 72 was fixed at a potential of −0.7 V. vs. reference electrode 74, the counter electrode 76 was driven on demand to supply current to the cell as before, and the current or signals from the two active testing electrodes were read out independently. The signals were then calibrated as before, and the resulting calibrated signals were fed to the strip recorder and readout as shown in FIG. 16, line IV a and IV b indicating the ability of the system of discriminate against methyl-L-dopa.

EXAMPLE IV

This example illustrates how the electrochemical detection cell made in accordance with the present invention may advantageously be employed as a screen. For this example, the active testing electrode at the leading edge of the flow (i.e. electrode 68) was set at a potential below the wave of the species of interest, while the other active testing electrode 72 was set at a potential at the wave of the species of interest. The signal from electrode 68 was discarded, while the signal from electrode 72 was passed to a logic module, a signal applied for multiple calibration purposes, and the signal from the calibration circuit was then fed to the strip recorder and readout as shown in FIG. 16, line V. One skilled in the art will recognize that under these aforesaid conditions electrode 68 will effectively screen or clean the eluant solution of all electroactive materials other than that of interest.

As should be clear from the foregoing the electrochemical detection apparatus of the present invention offers a number of advantages over prior art electrochemical detectors.

It is to be appreciated that the invention is not limited to application to liquid chromatograpy, but, rather the electrochemical detection apparatus may also be employed to monitor and/or measure the progress of a gas chromatographic separation process. In this regard, in some cases it may be possible to measure concentration or constitutional changes in the gases directly. In other cases it will be necessary to carry out the method in the presence of a liquid, preferably an electrolyte, e.g. by dissolving the eluant gas from the gas chromatography apparatus in an electrolyte and passing the electrolyte through the electrochemical detection cell.

Furthermore, the electrochemical detection apparatus is not limited to use with chromatography separations, but may also be advantageously employed for monitoring or directly measuring a variety of sample solutions, for example, of industrial, environmental, geophysical and biomedical interest. For example, the electrochemical detection apparatus of the present invention may be employed to provide on-line monitoring of a chemical process flow stream or a public water supply system, or for monitoring effluent from a sewage treatment facility.

Moreover, the electrochemical detection apparatus made in accordance with the instant invention is not limited to measuring only those compounds capable of undergoing electrochemical reactions, but also is capable of capacitive monitoring streaming solutions. For example, for measuring electrochemically non-reactive materials, a repetitive pulse of short duration e.g. 10 to 20 μsec., may be fed to current amplifiers 200 and 202, and a capacitive spike accumulated in signal accumulator 216 for a period of time, e.g. 100 to 500 μsec. prior to the calibration and recording. In this way any substance capable of changing the capacitance of the electrode double-layer can be seen at the signal output.

Still other features, modifications, advantages and objects will be obvious to one skilled in the art.

I claim:

1. A flow cell for electrochemical testing a sample in solution, said cell comprising:

a holder assembly having an inlet for directing a stream of said sample to be tested into said cell, and an outlet for directing tested sample from said cell;

a plurality of electrode elements arranged in a stack in said holder assembly and including at least one active testing electrode, at least one reference electrode, and at least one counter electrode, at least one of said active testing electrodes comprising a solid phase electrode in the form of a solid disk of electrically conductive material having at least one bore extending therethrough and having an active electrode surface located in said at least one bore, said plurality of electrodes being arranged in said stack so that said electrodes are electrically insulated from one another with their respective bores aligned so as to define at least one flow channel connecting said inlet and said outlet; and, a flow restrictor formed of electrically conductive material located in the bore of at least one of said disks and electrically connected to said disk.

2. A flow cell according to claim 1, wherein at least two of said plurality of electrodes comprise solid phase electrodes in the form of substantially flat generally round disks, and said bores are formed through the approximate centers of each of said disks.

3. A flow cell according to claim 1, comprising at least three electrode elements, at least one of said elecrode elements being an active testing electrode, and including means for connecting said active testing electrodes to controlled testing potentials; at least one other of said electrode elements being a reference electrode, and including means connecting said reference electrodes to a reference potential; and at least yet one other of said electrode elements being a counter electrode, and including means connecting said counter electrodes to yet another potential.

4. A flow cell according to claim 3, wherein at least one of said active testing electrodes comprises a disk of electrically conductive material in which the active surface area comprises wall areas of said disks subtending said bore.

5. A flow cell according to claim 4, wherein at least one of said disks comprises a metal disk.

6. A flow cell according to claim 4, wherein at least one of said disks comprises a graphite disk.

7. A flow cell according to claim 6, wherein said wall areas of said at least one graphite disk are coated at least in part with solid phase active electrode material.

8. A flow cell according to claim 7, wherein said solid phase active electrode material is selected from the group consisting of mercury, gold, silver, bismuth, $PbO_2$ and $MnO_2$.

9. A flow cell according to claim 3, and including a plurality of solid phase active testing electrode elements, and means connecting at least some of said plurality to different testing potentials.

10. A flow cell according to claim 3, wherein said reference electrode element comprises a salt-bridge medium located in said bore.

11. A flow cell according to claim 3, wherein said reference electrode element comprises an inert metal terminal.

12. A flow cell according to claim 3, wherein said reference electrode element comprises a metal or metal oxide terminal selected from the group consisting of palladium, palladium oxide and platinum.

13. A flow cell according to claim 12, wherein said reference electrode element comprises a disk of electrically insulating material in which surface areas on said disk subtending said bore are coated at least in part with said metal or metal oxide.

14. A flow cell according to claim 3, wherein said reference electrode element comprises at least one wire terminal formed of a metal oxide, and extending into said bore.

15. A flow cell according to claim 3, wherein at least one of said electrodes selected from the group consisting of said active testing electrodes and said counter electrodes comprises a disk of electrically insulating material in which the surface areas of said disk subtending said bore are coated at least in part with solid phase active electrode material.

16. A flow cell according to claim 15 wherein said solid phase active electrode material is selected from the group consisting of mercury, gold, silver, bismuth, $PbO_2$ and $MnO_2$.

17. A flow cell according to claim 3 wherein said reference electrode comprises an inert metal or metal oxide terminal.

18. A flow cell according to claim 17 wherein said inert metal or metal oxide terminal is selected from the group consisting of palladium, palladium oxide and platinum.

19. A flow cell according to claim 1, wherein said flow restrictor is located in the bore of at least one of said active testing electrodes.

20. A flow cell according to claim 1, wherein said flow restrictor comprises a solid body shaped in the form of a truncated tetrahedron, with a sharp point thereof facing said inlet.

21. A flow cell according to claim 1, including spacers formed of electrically insulating material located between at least some of said electrode elements, said spacers each having at least one bore extending therethrough and aligned with said flow channel.

22. A flow cell according to claim 1, wherein at least some of said electrode elements are coated at least in part with an electrically insulated material, and said bore extends through said coating.

23. In a chromatography apparatus having a chromatographic column through which a sample can be passed whereby species in said sample are separated to produce an eluant fluid stream, an electrochemical detector for analyzing said eluant stream, the improvement wherein said detector comprises a flow cell as defined by claim 1.

24. In a chromatography apparatus having a chromatography column through which a sample can be passed whereby species in said sample are separated to produce an eluant fluid stream, an electrochemical detector for analyzing said eluant stream, the improvement wherein said detector comprises a flow cell as defined by claim 23.

25. In a chromotography apparatus according to claim 23 or claim 24 wherein said fluid comprises a liquid carrier stream.

26. In a chromatography apparatus according to claim 23 or claim 24 wherein said fluid comprises a gas carrier stream.

27. A flow cell for electrochemically testing a sample stream, said cell comprising in combination:
a holder assembly having an inlet for directing said stress to be tested into said cell, and an outlet for directing tested sample from said cell;
at least one reference electrode comprising a flat solid body mounted in said holder assembly, said body having (a) a pair of generally planar surfaces, (b) a bore extending therethrough between said planar surfaces, and (c) an active electrode surface located within said bore;
at least one counter electrode comprising a flat solid body mounted in said holder assembly, said body having (a) a pair of generally planar surfaces, (b) a bore extending therethrough between said planar surfaces and (c) an active electrode surface located within said bore;
at least one active testing electrode comprising a solid phase electrode in the form of a flat solid body mounted in said holder assembly, each of said bodies having (a) a pair of generally planar surfaces (b) a bore extending therethrough between said planar surfaces, (c) solid phase active electrode surface located within said bore; and, (d) a plug of porous, electrically conductive material located in the bore of at least one of said bodies and electrically connected to said body;
said at least one reference electrode, said at least one counter electrode, and said at least one active testing electrode being mounted in said holder assembly electrically insulated from one another with their respective bores aligned with one another so as to define a flow channel between said inlet and said outlet.

28. An electrochemical testing apparatus for measuring a sample material in solution comprising:
a flow cell having at least one flow path therethrough, an inlet for directing a stream containing said sample material to be tested into said cell, and an outlet for directing tested sample material from said cell;
a plurality of electrodes including at least one solid phase testing electrode located in said at least one flow path, each of said electrodes having at least one bore extending therethrough and forming a boundary or boundaries for said at least one flow path, said electrodes being positioned in serial arrangement along said at least one flow path;
a plug of porous, electrically conductive material located in the bore of at least one of said solid phase testing electrodes and electrically connected to said electrodes; and,
means connecting at least said at least one solid phase electrode to an active testing potential source; means connecting at least one other of said electrodes to a reference potential source; means connecting at least yet another of said electrodes to yet another potential source; and, means coupled to said means for connecting for producing an electrical signal readout representative of current flow between selected of said electrodes.

29. An electrochemical testing apparatus according to claim 28 wherein said reference electrode comprises an electrically non-conductive solid body with said bore extending therethrough and having a salt-bridge reference located in the bore in said body, and wherein said reference potential source comprises a constant current potential.

30. An electrochemical testing apparatus according to claim 28 wherein said reference electrode comprises an electrically non-conductive solid body with said bore extending therethrough and having an inert metal or metal oxide terminal located in the bore in said body, and wherein said reference potential source comprises a constant current potential source.

31. An electrochemical testing apparatus according to claim 30 wherein said inert metal or metal oxide terminal is selected from the group consisting of palladium, palladium oxide and platinum.

32. An electrochemical testing apparatus according to claim 28 wherein said reference electrode comprises an electrically non-conductive solid body with said at least one bore extending therethrough and having an inert metal or metal oxide terminal located within said at least one bore, and wherein said reference potential source comprises a feed back network and follower amplifier for applying a variable potential which is responsive to changes in said stream.

33. An electrochemical testing apparatus according to claim 32 wherein said inert metal or metal oxide terminal is selected from the group consisting of palladium, palladium oxide and platinum.

34. In a method of electrochemically analyzing a sample material to identify selected substances therein, the steps of: dissolving said sample material in a carrier therefor to form a test fluid, and passing a stream of said test fluid through an electrolytic flow cell in contact with a detection electrode, the improvement wherein said flow cell comprises a plurality of electrode elements including at least one solid phase testing electrode arranged in a stack in a holder, each of said electrode elements in said stack comprising a solid body having at least one bore extending therethrough and an active electrode surface located in said at least one bore, said plurality of electrodes being arranged in said stack so that said electrodes are electrically insulated from one another with their respective bores aligned so as to define at least one flow channel for said stream, said flow cell having a plug of electrically conductive material located in the bore of at least one of said solid phase testing electrodes and electrically connected to said electrode, passing said stream through said at least one flow channel in contact with said active electrode surfaces, applying electrical potentials across said stream between selected of said electrodes in said stack, deriving electrical signals resulting on selected of said electrodes in said stack, and sorting said signals to obtain signals which identify said selected substances.

35. In a method according to claim 34, including the step of deriving an electrical signal corresponding to charge transfer reactions of materials in said stream.

36. In a method according to claim 34, including the step of deriving an electrical signal corresponding to the electrical double layer of said stream.

37. In a method according to any one of claims 34, 35, or 36, wherein said carrier comprises a gas.

38. In a method according to any one of claims 34, 35 or 36, wherein said carrier comprises a liquid.

39. In a method according to claim 34 and including the steps of applying to at least one of said electrodes a controlled testing potential; applying to at least one other of said electrodes a reference potential; and applying to at least yet one other of said electrodes yet another potential.

40. In a method according to claim 39, and including the steps of sensing changes in said stream and varying said reference potential responsive to said changes in said stream.

41. In a method according to claim 34, including the step of passing said test fluid through a chromatography column whereby to separate species of said sample material to produce, an eluant fluid stream, and passing said eluant fluid stream through said flow cell.

42. A flow cell for electrochemically testing a sample in solution, said cell comprising:
a holder having an inlet for directing a stream of said sample to be tested into said cell, an outlet for directing tested sample from said cell, and a flow channel connecting said inlet and said outlet;
a plurality of electrode elements including at least one solid phase testing electrode, at least one reference electrode and at least one counter electrode, arranged in a stack in said holder, at least one of said electrode elements in said stack comprising a solid, porous body having active electrode surfaces located in the pores of said body, at least one other of said electrode elements in said stack comprising a solid body having at least one bore extending therethrough and having a plug of porous, electrically conductive material having active electrode surfaces located in said bores, said bores and said pores being aligned so as to define said flow channel in part.

43. A flow cell according to claim 42, comprising at least three electrode elements, at least one of said solid phase electrode elements being an active testing electrode, and including means for connecting said at least one active testing electrode to a controlled testing potential; at least one other of said electrode elements being a reference electrode, and including means connecting said at least one reference electrode to a reference potential; and at least yet one other of said electrode elements being a counter electrode, and including means connecting said at least one counter electrode to yet another potential.

44. A flow cell according to claim 43, and including a plurality of active testing electrode elements, and means connecting at least some of said plurality to different testing potentials.

45. A flow cell according to claim 44, wherein said reference electrode element comprises a metal or metal oxide terminal selected from the group consisting of palladium, palladium oxide and platinum.

46. A flow cell according to claim 45, wherein said reference electrode element comprises at least one wire terminal formed for said metal or metal oxide, and extending into said channel, and at least one other of said electrode elements in said stack comprises a solid body having at least one bore extending therethrough and having a plug of porous, electrically conductive material located in said bore and electrically connected to said body.

47. A flow cell according to claim 43, wherein said reference electrode element comprises an inert metal or metal oxide terminal.

48. A flow cell according to claim 42, wherein said plug is located in the bore of at least one of said active testing electrodes.

49. A flow cell according to claim 42, wherein said material comprises graphite.

50. A flow cell according to claim 42, and including solid phase active electrode material deposited in at least some of the pores of said plug.

51. A flow cell according to claim 50, wherein said solid phase active electrode material is selected from the group consisting of mercury, gold, silver, bismuth, $PbO_2$ and $MnO_2$.

52. A flow cell according to claim 42, including spacers formed of electrically insulating material located between at least some of said electrode elements, said spacers each having at least one bore extending therethrough and aligned with said channel.

53. A flow cell according to claim 42, wherein said holder comprises a solid body of polytetrafluoroethylene.

54. In a chromatography apparatus having a chromatographic column through which a sample can be passed whereby species in said sample are separated to produce an eluant fluid stream, and an electrochemical detector for analyzing said eluant stream, the improvement wherein said detector comprises a flow cell as defined by claim 42.

55. In a chromatography apparatus according to claim 54 wherein said fluid comprises a liquid carrier stream.

56. In a chromatography apparatus according to claim 54 wherein said fluid comprises a gas carrier stream.

57. In a method of electrochemically analyzing a sample material to identify selected substances therein, the steps of: dissolving said sample material in a carrier therefor to form a test fluid and passing a stream of said test fluid through an electrolytic flow cell in contact with said detection electrode, the improvement wherein said flow cell comprises a plurality of electrode elements including at least one solid phase testing electrode arranged in a stack in a holder, at least one of said electrode elements in said stack comprising a solid, porous having active electrode surfaces located in the pores of said, at least one other of said electrode elements in said stack comprising a solid body having at least one bore extending therethrough and having a plug of porous, electrically conductive material having an active electrode surface located in said at least one bore, said plurality of electrodes being arranged in said stack and electrically insulated from one another in said holder with said at least one bore and said pores being aligned so as to define at least one flow channel for said stream, applying electrical potentials across said stream between selected of said electrodes in said stack, deriving electrical signals resulting on selected of said electrodes in said stack, and sorting said signals to obtain signals which identify said selected substances.

58. In a method according to claim 53, including the step of deriving an electrical signal corresponding to charge transfer reactions of materials in said stream.

59. In a method according to claim 57, including the step of deriving an electrical signal corresponding to the electrical double layer of said stream.

60. In a method according to any one of claims 57, 58, or 59, wherein said carrier comprises a gas.

61. In a method according to any one of claims 57, 58 or 59, wherein said carrier comprises a liquid.

62. In a method according to claim 57, and including the steps of applying to said at least one solid phase testing electrode a controlled testing potential; applying to at least one other of said electrodes a reference potential; and applying to at least yet one other of said electrodes yet another potential.

63. In a method according to claim 62, and including the steps of sensing changes in said stream and varying said reference potential responsive to said changes in said stream.

64. In a method according to claim 57, including the step of passing said test fluid through a chromatography column whereby to separate species of said sample material to produce an eluant fluid stream, and passing said eluant fluid stream through said flow cell.

65. An electrochemical apparatus for testing a sample material in solution, said apparatus comprising, in combination:

an electrolytic cell for holding said sample to be tested, said electroyltic cell having a plurality of electrically discrete electrodes located therein, at least one of said plurality comprising a solid phase active testing electrode, at least one other of said plurality comprising a counter electrode, and at least one other of said electrodes comprising a reference electrode, wherein at least one of said electrodes selected from the group consisting of said active testing electrode and said counter electrode comprises a plug of porous, electrically conductive material, and said reference electrode comprises an inert metal or metal oxide terminal, and including means connecting said solid phase active testing electrode to an active testing potential source; means connecting said at least one counter electrode to yet another potential source, and means connecting said at least one reference electrode to a feed back network and follower amplifier for applying a variable potential which is responsive to electrochemical changes in said sample.

66. An electrochemical apparatus according to claim 65 wherein said reference electrode comprises an inert metal or metal oxide terminal selected from the group consisting of palladium, palladium oxide and platinum.

67. An electrochemical flow cell for testing a sample material in solution, said apparatus comprising, in combination:

a holder assembly having an inlet for directing a stream of said sample to be tested into said cell, and an outlet for directing tested sample from said cell;

a plurality of electrically discrete electrodes located in a stack in said holder assembly, said plurality including at least one solid phase active testing electrode, at least one counter electrode, and at least one reference electrode, at least one of said solid phase active testing electrodes in said stack comprising a solid body having at least one bore extending therethrough and defining in part a flow channel connecting said inlet and said outlet, a plug of porous, electrically conductive material located in said flow channel in said at least one bore, and including means connecting said at least one solid phase active testing electrode to an active testing potential source, means connecting said at least one counter electrode to yet another potential source, and means connecting said at least one reference electrode to a feed back network and follower amplifier for applying a variable potential which is responsive to electrochemical changes in said sample.

68. An electrochemical flow cell according to claim 67 wherein said reference electrode comprises an inert metal or metal oxide terminal selected from the group consisting of palladium, palladium oxide and platinum.

* * * * *